(12) United States Patent
Tewfik et al.

(10) Patent No.: US 10,026,016 B2
(45) Date of Patent: Jul. 17, 2018

(54) TRACKING AND REPRESENTATION OF MULTI-DIMENSIONAL ORGANS

(75) Inventors: Ahmed H. Tewfik, Edina, MN (US); Dan Wang, Minneapolis, MN (US); Timothy Kinney, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 2243 days.

(21) Appl. No.: 12/822,065

(22) Filed: Jun. 23, 2010

(65) Prior Publication Data

US 2011/0044521 A1 Feb. 24, 2011

Related U.S. Application Data

(60) Provisional application No. 61/220,888, filed on Jun. 26, 2009.

(51) Int. Cl.
| | |
|---|---|
| G06Q 50/00 | (2012.01) |
| G06K 9/62 | (2006.01) |
| G06T 7/246 | (2017.01) |
| G06Q 10/00 | (2012.01) |
| G16H 30/40 | (2018.01) |
| A61B 1/00 | (2006.01) |
| G06K 9/32 | (2006.01) |

(52) U.S. Cl.
CPC ......... *G06K 9/6232* (2013.01); *G06K 9/6206* (2013.01); *G06T 7/251* (2017.01); *A61B 1/00009* (2013.01); *G06K 2009/3291* (2013.01); *G06K 2209/051* (2013.01); *G06T 2207/10016* (2013.01); *G06T 2207/10072* (2013.01); *G06T 2207/20081* (2013.01); *G06T 2207/30084* (2013.01); *G16H 30/40* (2018.01)

(58) Field of Classification Search
CPC .................. G06T 7/0012; G06T 7/0083; G06T 2207/30004; G06T 7/0081; G06F 19/321
USPC ......................................................... 382/128
See application file for complete search history.

(56) References Cited

U.S. PATENT DOCUMENTS

| | | | |
|---|---|---|---|
| 7,363,198 B2 | 4/2008 | Balaniuk et al. | |
| 7,467,075 B2 | 12/2008 | Humphries et al. | |
| 7,526,112 B2 | 4/2009 | Murphy et al. | |
| 7,536,042 B2 | 5/2009 | Murphy et al. | |
| 7,538,764 B2 | 5/2009 | Salomie | |
| 7,573,461 B2 | 8/2009 | Rosenberg | |
| 7,646,901 B2 | 1/2010 | Murphy et al. | |
| 7,680,300 B2 | 3/2010 | Chang et al. | |
| 2010/0013860 A1 | 1/2010 | Mandella et al. | |
| 2010/0026789 A1 | 2/2010 | Balogh | |

OTHER PUBLICATIONS

Huang, Spatio-Temporal Modeling Method for Shape Representation, 3D Data Processing, 3DPVT 2006.*

(Continued)

*Primary Examiner* — Tran N Nguyen
(74) *Attorney, Agent, or Firm* — Schwegman Lundberg & Woessner, P.A.

(57) ABSTRACT

A method includes receiving data corresponding to a sequence of deformations of a surface of an object. The method also includes generating spherical harmonics expressions based on the data. The method includes identifying a subspace of the spherical harmonics expression corresponding to the surface.

12 Claims, 4 Drawing Sheets

(56) References Cited

OTHER PUBLICATIONS

Chentanez, N., et al., "Interactive Simulation of Surgical Needle Insertion and Steering", *Proceedings of ACM SIGGRAPH 2009*, (Aug. 2009), 88:1-88:10.

Di, Y., et al., "Moving Mesh Methods for Singular Problems on a Sphere Using Perturbed Harmonic Mappings", [online]. Retrieved from the Internet: <http://www.cscamm.umd.edu/publications/sphere_CS-06-05.pdf>, (Mar. 14, 2006), 1-23.

English, J., et al., "Visual Tool Tracking for Open Surgery Simulation and Training", [online]. [archived Nov. 11, 2006]. http://wayback.archive.org/web/20061115000000*/http://www.energid.com/5342116002416779827131181346/link.htm>, (2006), 8 pgs.

Liu, A, et al., "A Survey of Surgical Simulation", *Applications, Technology, and Education, Presence*, vol. 12, Issue 6, (Dec. 2003), 45 pgs.

Petterssson, J., "Automatic Generation of Patient Specific Models for Hip Surgery Simulation", Linköping Studies in Science and Technology Thesis No. 1243, Institute of Technology, Linköping University, (Apr. 2006), 94 pgs.

Santhanam, A. P., "Modeling, Simulation, and Visualization of 3D Lung Dynamics", PhD Dissertation, School of Electrical Engineering and Computer Science, University of Central Florida, Orlando, (2006), 204 pgs.

Santhanam, A. P., "Simulating 3D Lung Dynamics Using a Programmable Graphics Processing Unit", *IEEE Transactions on Information Technology in Biomedicine*, 11(5), (Sep. 2007), 497-506.

Wang, Y., "3D Harmonic Mapping and Tetrahedral Mapping and Tetrahedral Meshing of Brain Imaging Data", [online]. Retrieved from the Internet: <URL: http://www.loni.ucla.edu/~thompson/MICCAI2004/YW_MICCAI2004v3.pdf>, (2004), 8 pgs.

Wang, Y., et al., "Volumetric Harmonic Brain Mapping", *IEEE International Symposium on Biomedical Imaging: Macro to Nano (ISBI '04)*, (2004), 1275-1278.

Wang, Y., et al., "Volumetric Harmonic Map", *Communications in Information and Systems*, 3(3), (Mar. 2004), 191-202.

\* cited by examiner

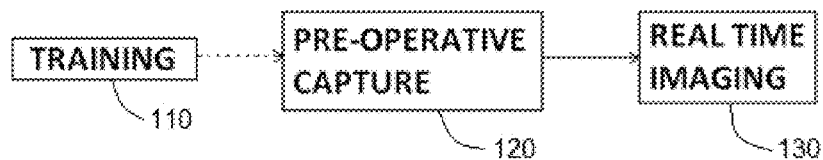
FIG. 1
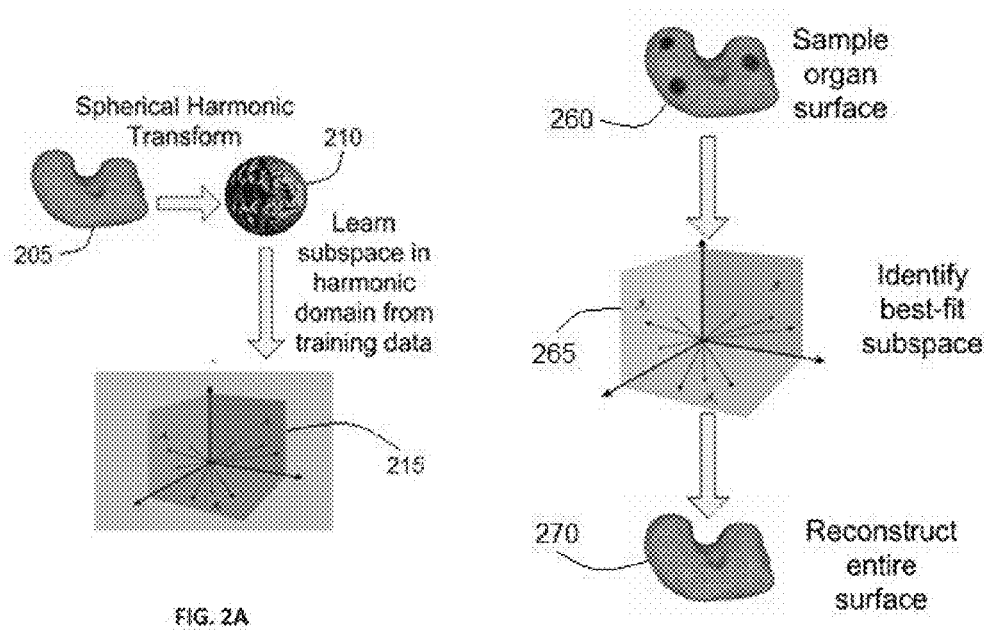
FIG. 2A
FIG. 2C

TRACKING AND REPRESENTATION OF MULTI-DIMENSIONAL ORGANS

CLAIM OF PRIORITY

This patent application claims the benefit of priority, under 35 U.S.C. Section 119(e), to Ahmed H. Tewfik et al., U.S. Provisional Patent Application Ser. No. 61/220,888, entitled "TRACKING AND REPRESENTATION OF MULTI-DIMENSIONAL ORGANS," filed on Jun. 26, 2009, and is incorporated herein by reference.

BACKGROUND

In a minimally invasive surgical (MIS) procedure, a small orifice in the body provides access to internal organs. MIS procedures have led to shorter hospitalizations and lower morbidity and mortality. For patients, this translates to less pain and suffering, smaller scars, and quicker return to normal activities.

Minimally invasive surgical (MIS) procedures include laparoscopic surgery and natural orifice translumenal endoscopic surgery, (NOTES). NOTES involves approaching the abdominal cavity (or other body cavities) through natural orifices such as the mouth or vagina, without creating an incision on the abdominal wall. Surgery is performed through this single natural orifice using a flexible endoscope.

Several challenges make MIS procedures particularly difficult. One challenge is the narrow field of view and lack of depth perception with these techniques. During an open procedure, the surgeon can view the surgical field from different angles and perspectives and the haptic feedback provides a mental three-dimensional (3D) image. Laparoscopy, for example, involves inserting a laparoscopic camera through a separate port for accessing the abdominal cavity from various angles of approach to the target area. The exact relative location of the tip of the endoscope relative to nearby anatomic structures must be accurately known in minimally invasive procedures since surgical targets lie in a retrograde position with respect to the single incision made in these procedures. Determining this position is complicated by the flexibility of the tip of the endoscope that makes it difficult to track its distal orientation.

Pre-operative magnetic resonance imaging (MRI) or computed tomography (CT) scans do not solve the restricted visualization problem in MIS surgery. The actual intra-operative scene differs from pre-operative imagery due to several factors, including patient positioning, gas insufflation to create a working space, tool-tissue interaction, and body movements (such as breathing and heart beat).

Current imaging techniques for MIS procedures are either too complex for real time implementation, require information that may not be readily available, or do not provide the resolution and accuracy needed to avoid complications during surgery.

OVERVIEW

An example of the present subject matter provides a high resolution, real time, 3D view of an organ as it is deformed during surgery. The video signal acquired with a limited field of view 3D laparoscopic, endoscopic camera, or other camera is combined with a pre-operative MRI or CT scan to display intra-operative, 3D organ images on a computer screen. The real time 3D imagery allows the surgeon to see into an organ or adipose tissue during surgery rather than just look at its surface.

An organ surface can be characterized by a method including identifying subspaces in combination with spherical harmonic representations. The organ surfaces (both exterior and interior) can be tracked in real time using sparse sampling of the exterior surfaces.

Training data can be generated and used to construct dictionaries and identify subspaces. The data can be generated using magnetic resonance imaging (MRI), computerized tomography (CT), computer modeling or other imaging modality. An in vivo organ can be sampled (imaged) using a needlescope, an endoscope or a laparoscope.

According to one method, training data is processed using a spherical harmonic transform, as well as subspace pursuit and clustering, to provide a compact surface representation.

In addition, a sampling strategy is designed. A sampling location is determined by forming an over-determined linear system to be solved with small condition number. The sampling strategy can include global sampling, patch sampling, or localized sampling. The sampling strategy is implemented using a needlescope, an endoscope, a laparoscope or other imaging modality.

Furthermore, organ deformation can be reconstructed and displayed on a visual monitor. A subspace is selected where the deformation best fits to reconstruct the whole surface using the samples taken using the sampling strategy. The surface can be reconstructed using the selected subspace.

An example of the present subject matter can be used for fast simulation of the surface deformation (exterior, interior, or both) of an organ. In addition, an example can be used to reconstruct a single ex vivo organ deformation using training data from that organ.

Training can be conducted using data from a single subject or from multiple different subjects.

The training data, in combination with intra-operative restricted field of view optical data and a single pre-operative MRI/CT scan, can be used to characterize an organ.

Spherical harmonics representation can include orthogonal basis in spherical coordinates having the form $$Y_{l,m}(\theta, \phi) = (-1)^m \sqrt{\frac{2l+1}{4\pi}} \sqrt{\frac{(l-m)!}{(l+m)!}} P_{l,m}(\cos\theta)e^{im\phi}.$$

In addition, spherical harmonics representation can also include a parametric description having the form $$f(\theta, \phi) = \sum_{l=0}^{\infty} \sum_{m=-l}^{l} f_{l,m} Y_{l,m}(\theta, \phi)$$

Spherical parameterization entails creating a bijective mapping from a surface $f(x,y,z)$ to a sphere $S(\theta,\varphi)$ by minimizing area, length or angle distortion.

Training can involve an iterative process including: representation of a training vector; identify sparsest in terms of all others, identify orthogonal subspace to space spanned by vectors selected to represent initial vector, remove from data set all vectors orthogonal to that subspace, and reduce dictionary size by examining principal angles and vectors of pairs of subspaces Subspace clustering can include using an orthogonal least squares sparse representation algorithm. This entails orthogonalize remaining dictionary elements after each step. In addition, subspace clustering can include eliminating spurious subspaces. This can entail re-clustering data among identified subspaces and eliminating subspaces corresponding to small clusters. In addition, this can include optimizing remaining subspaces if desired using SVD.

Registration of the data during training can include a linear translation and rotation estimation. This can take the form of $$f(R_r, T_t) = \frac{1}{N_p} \sum_{i=1}^{N_p} \|\vec{q}_i - R_r \vec{p}_i - T_t\|^2.$$

In addition, registration can also include implementation of iterative closet point (ICP) algorithm which terminates when mean square distance achieves a predetermined minimum.

Surface correspondence can include a pixel-wise alignment tailored to minimize a distance between SH coefficient pairs. Pixel-wise alignment can take the form:

$$RMSD = \sqrt{1/4\pi \sum_{l=1}^{(L+1)^2} \|f_{t,l} - f_{k,l}^0\|^2}$$

Registration during tracking is configured to register optical images with the initial training model. Tracking registration entails eliminating transformation between pre-operative MRI/CT model and the optical device. This can include any combination of feature point method and ICP refinement. During ICP iterations, numbers pairs of samples are automatically taken from the two surfaces and are used to refine the registration result.

Tracking registration can include a fine tuning procedure. Fine tuning can eliminate observed transformation by 'neighbor searching.' Neighbor searching entails reconstructing observed patch by hypothesizing location and by selecting a location that yields a minimum error. For example, a series of intersecting regions on a surface of an organ may be found to represent a defined neighborhood, an initial sampling location, a shifted sampling location and a determined location having a local minimum error.

The sampling strategy is selected to yields a well-conditioned subspace identification and spherical harmonic coefficient estimate (surface reconstruction).

Spherical harmonic representation coefficients of an organ surface lie in lower dimensional subspaces. Training data can be used to learn subspaces in harmonic domain.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1 includes a block diagram showing a training phase, pre-operative data capture, and real time imaging.

FIG. 2A illustrates a method for subspace learning (in training).

FIG. 2B illustrates a flow chart of a method for training.

FIG. 2C illustrates subspace identification and organ reconstruction during surgery.

DETAILED DESCRIPTION

Part I—Surface Representation and Reconstruction

Figure 3A:
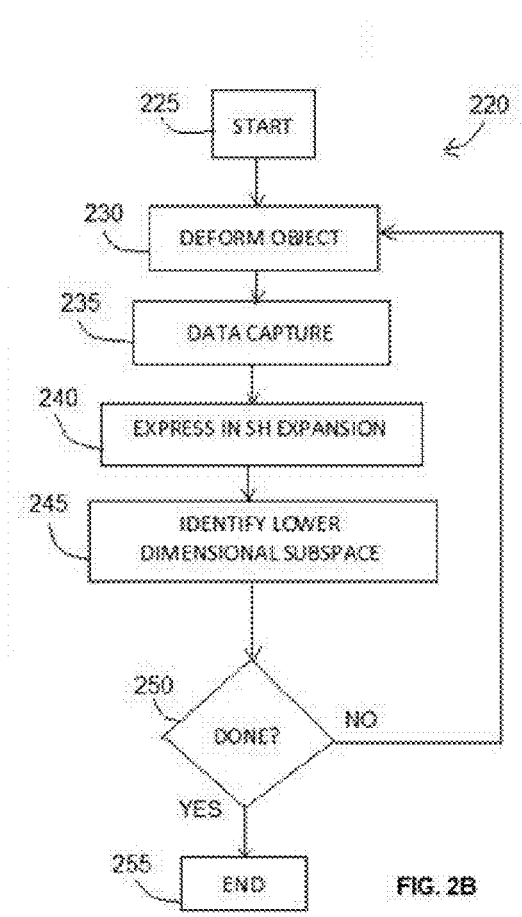
FIGS. 3A, 3B, and 3C illustrate different sampling strategies.
Figure 3A:
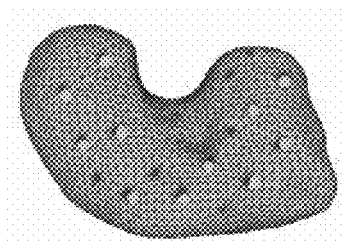

An example of the present subject matter includes capturing variations in organ shapes based on accurate surface representations. For example, parametric 3D surface descriptors can be used in shape modeling based on harmonic functions, such as hyperquadrics and superquadrics. Spherical harmonics (SH) is one such method and provides smooth, fine-scale shape representation with high approximation accuracy. The level of retained surface details is controlled by the number of harmonics applied in the representation. A SH representation of a 3D surface with no hole (genus zero surface), projects the organ surface onto an enclosing sphere and represents the (x, y, z) coordinates of each point on the original surface as a function of its projected 2D angular position onto the sphere using spherical harmonics. The mapping is invertible and minimizes distortion due to the projection.

Spherical harmonics can be applied to 3D kidney modeling and registration. A weighted Fourier series (WFS) representation for cortical surfaces can be used to add exponential weight to each harmonic in order to converge quickly and reduce ringing artifacts. A surface matching algorithm based on SH description can be used in cardiac MRI analysis. A spatial-temporal modeling method can be used to represent the dynamic anatomical structure of an organ with periodic motion such as a beating heart.

Such examples are suitable for use with static models, without considering the surface deformation of the underlying object, are tailored specifically for certain organs with specific properties or known periodic motions, and are not generally applicable.

For example, one approach relies on the time-dependent spherical harmonics that are solutions to the wave equations, given the prior information about the motion cycle of the organ. Another method specifically aims to model the deformation of lungs and viscera induced by breathing. Numerous markers are stuck on the patient's skin to predict the organ deformation from preoperative CT images. One approach entails a spatio-temporal adaptive sampling strategy for modeling dynamic viscoelastic deformable objects. These and related methods are too costly in terms of both computation time and memory space for real time 3D organ deformation tracking.

Sparse surface and internal structure representations can be used in reconstruction methods based on limited view data from the surface of the organ.

The present subject matter includes a method for learning sparse structured representations in the form of linear subspaces from data. A linear subspace is a set of vectors closed under addition and scalar multiplication. Data lies in a linear subspace if, when viewed as a vector, it can be expressed as a linear combination of the vectors that form a basis of the subspace.

An example of the present subject matter, called iterative subspace learning (ISI), identifies the subspaces where the data lives by finding the sparsest representation of each training vector in terms of the other vectors in the training data sets. Next, a clustering (i.e., vector quantization) operation is used to identify all observations that live in the same subspace. The dictionary design method offers computational savings relative to K-SVD for similar performance and better generalizability when evaluated on data beyond the training set.

Compressed sensing, on the other hand, seeks to acquire signals that are known to have sparse representations in a known domain using a minimal number of measurements. However, compressed sensing theory requires that the measurements be random linear combinations of the signal samples (e.g., surface pixels) which is a difficult requirement to satisfy. Furthermore, compressed sensing theory requires more observed data than the present subject matter because it does not exploit the structure of the sparse representation.

Approaches for 3D scan completion or surface inpainting may be used to fill small holes existing in scanned data. Example-based approaches can recover relatively large missing portion using patch warping and stitching from an extensive 3D model library. However, these approaches also require that the majority of the surface information be available. Furthermore, warping and matching procedures are too computationally demanding to be implemented in real-time.

In contrast, an example of the present subject matter identifies a specific, structured, sparse representation of the 3D organ surface that matches the very limited observed data and is suitable for a naturally shaped or a deformed organ. The structured sparse surface representation is selected from a set of possible sparse structured surface descriptors learned from training data. The procedure can accurately reconstruct arbitrary organ deformations with high accuracy, in real time, and based on a limited observed data set.

FIG. 1 illustrates a block diagram showing a training phase (110), pre-operative data capture or imaging (120), and real time imaging (130). Training 110 can include constructing dictionaries and identifying subspaces using MRI, CT scans, ultrasound, or modeling. Training can occur at a time before the pre-operative data capture as denoted by the dotted arrow line in the figure. Pre-operative data capture or imaging 120 can include constructing an initial model using CT or MRI scan. Real time imaging 130 can include live, 3D organ tracking.

The mechanical properties of an organ will limit the number of ways in which that organ will deform. One example of the present subject matter can be used to identify sparse and structured representations that can represent an arbitrary deformation of the entire surface and interior structures of an organ. Sparse structured representations can be used to reconstruct arbitrary deformations of the surface of the organ or any interior structure using limited surface data acquired using a restricted view 3D probe.

The probe can be based on optical, ultrasound or other modality. Some examples discussed herein consider the use of optical means for tracking organ or tissue deformation. Rather than produce a dictionary of all possible surface deformations, an example of the present subject matter uses limited training data acquired from different subjects to learn the structured sparse representations.

As such, an example of the present subject matter provides organ surface reconstruction and internal structure visualization with an average accuracy of 2.1 mm based on a limited optical field of 12 mm×15 mm.

Living and moving 3D images can provide visualization of the target organ and surgical bed. Such images can be used to augment the virtual reconstructed imaging presented herein for purposes of improving safety and accuracy in surgical procedures.

An example of the present subject matter can be used for simulation, planning, and training with high fidelity and in real time. Such results enable fast organ segmentation methods based on MRI or CT scans with minimal operator input.

Furthermore, the time resolution of CT, MRI, and 3D ultrasound scans can be increased by interpolating frames in between recorded frames using one example of the present subject matter.

Real Time Tracking of 3D Organ Surfaces

An example of the present subject matter provides 3D, real time, surface reconstruction and includes methods for the registration of training imagery corresponding to different individuals and a mix of modalities suitable for surgical simulation.

A 3D organ surface can be reconstructed using limited views provided three criteria are met. First, the surface representation must be learnable from a small set of organ 3D surface samples obtained from, for example, MRI or CT scans from different subjects. A small set of learned, sparse structured representations can represent an arbitrary deformation of the organ.

Second, the surface representation must be sparse to allow reconstruction of the organ from a limited field of view of 3D endoscopic scanners. The limited field of view may be less than 10% of the organ surface and leads to a small number of equations in the unknown coefficients of the surface representation. If the number of such unknown coefficients is smaller than the number of equations (e.g., when the representation is sparse), the organ surface can be reconstructed from the limited field of view.

Third, the representation should have a known structure since it can then yield a reconstruction method that is resilient to measurement uncertainty.

Consider an example using surgically excised porcine organs. The organs can be manually manipulated (to mimic surgical maneuvers) and organ deformation can be tracked using optical, MRI or CT images. For example, the liver edge and gallbladder can be lifted and retracted with grasping forceps and retractors. The deformation is maintained using non-magnetic mechanical set-ups and can be quantified using fiducial points (on the organ surface) and targets (inserted in the organs).

Video of these manipulations can be recorded and reference points from these images can be used to track organ movement and deformation. Various angles of approach for capturing the video footage can be used, and various reference points can be tracked.

For each deformation, the excised organ is passed through the CT scanner and/or MRI scanner and 3D reconstructed images are created. These MRI or CT scans serve as the ground truth against which reconstructions are compared. The organs can be examined using laparoscopic and endoscopic 3D optical imaging.

Consider an ex vivo procedure using three porcine kidneys. A portable 3D laser scanner having 0.38 mm resolution can be used to acquire 3D optical data in real time from a small patch on one side of the kidney under investigation. The size of the optical patch used for reconstruction and collected with the optical camera on the scanner can be approximately 12 mm×15 mm. The kidneys can be deformed arbitrarily in a controlled manner and the deformation maintained using a non-magnetic mechanical device. The deformed kidney can be scanned in 3D MRI mode using a 1.5 Tesla MRI system with isotropic spatial resolution of 1.2 mm in each direction, producing 128×128×128 voxel images.

Arbitrary Organ Surface Deformations

FIG. 2A illustrates a method for learning. As shown in the figure, during training, 3D organ surfaces obtained from MRI or CT scans can be represented using SH expansions. The SH coefficients of an organ surface lie in specific low dimensional subspaces. One or more of lower dimensional subspaces of the SH coefficients (corresponding to the x, y and z coordinates of the surface) can be identified. Each subspace can be used to express the SH coefficients corresponding to a set of surface deformations as linear combinations of the basis vectors of the subspace. In the figure, organ 205 represents a specimen used for training, and in one example, organ 205 is manipulated to deform a surface. At 210, data from organ 205 is transformed using spherical harmonics. At 215, a subspace is learned from the training data.

A single subspace is sufficient to represent each of the x, y and z coordinates for all deformations of an organ. An iterative subspace identification (ISI) method is used to learn the subspaces. For each subspace to be learned, the method is given a number of training samples larger than the dimensionality of the subspace plus one. The ISI method does not require a prior knowledge of the number or dimensionality of the subspaces. These are identified from the training data. In the absence of a priori the number of subspaces and their dimensionality, collect a large number of training 3D MRI or CT scans. The ISI method uses the SH coefficients corresponding to the data.

Data collection proceeds until the data falls in the subspaces identified by the ISI method within the desired accuracy level and includes a number of samples that is larger than the largest of the sums of the dimensionalities of the subspaces corresponding to each of the three coordinates of points on the organ surface.

FIG. 2B illustrates iterative training method 220. At 225, the method begins. At 230, training includes deformation of an object. At 235, data is captured. The data capture can be accomplished using model data, ultrasound data, computerized tomography (CT), or magnetic resonance imaging (MRI) data. At 240, the data is expressed in an SH expansion. At 245, a lower dimensional subspace is identified. At 250, an inquiry is presented to determine if the iterative process is finished. If not yet done, processing continues with another deformation of the object. If finished, the training process concludes at end 255.

FIG. 2C illustrates reconstruction. For reconstruction of 3D surfaces during live surgery, each voxel obtained from the laparoscopic or endoscopic 3D camera is used to write an equation in the unknown subspace coefficients that determine the SH coefficients of the three coordinates of all points on the organ surface. The coefficients corresponding to the subspace can be reconstructed provided that the number of voxels is larger than the number of such coefficients for each possible subspace that can be used to describe a set of organ surface deformations within the desired accuracy.

Scanning data for approximately 10% of an organ surface is sufficient for reconstruction. The subspace that provides the minimum reconstruction error at all voxels obtained from the camera is then retained as the subspace that best represents the current deformation. The coefficients corresponding to that subspace are then used to reconstruct the entire surface. The number of samples required for 3D surface reconstruction is less than the number of samples that can be captured using a 3D endoscopic camera.

A sample selection strategy is implemented that minimizes the condition number of the set of linear equations to be solved to identify the correct subspace and ultimately reconstruct the entire surface. The selection method selects sets of voxels randomly and retains the set that offers the least condition number. This enhances robustness to noise and approximation errors. This approach can be applied to kidney samples and other organs, including the gallbladder, pancreas and liver.

In the figure, a surface of organ 260 is sampled. At 265, the best-fit subspace is identified. In other examples, the fit is not best-fit but instead, is good fit. At 270, the entire surface is reconstructed. This can include an exterior surface as well as an interior surface.

Consider organ tracking in the context of a complex brain surface and two gallbladders.

3D cortical mesh data for a brain surface can be used to generate multiple deformations of an initial brain surface. The deformations can be generated with software using a simulation open framework architecture. The software can be configured to implement a finite element (FE) method to generate deformations.

According to one experiment, 35 deformations can be tracked during training. The simulations can be performed on a processor running at 1.2-GHz laptop with 1-GB memory. Each brain mesh can include 40962 points and spherical harmonics up to degree 80 can be used for approximation. Based on the training deformations, deformation subspaces can be identified using the ISI approach. The brain surface can be reconstructed by monitoring 29 sample positions. Using these parameters, the subspace matrices can be stored in 9 MB and each deformed surface can be reconstructed in milliseconds. The milliseconds processing time of the present subject matter and the small number of surface samples (29) enable 3D real time organ tracking using limited views.

Gallbladder data can be generated by a mass-spring surgical simulator. The surgical simulator incorporates a volumetric force to mass-spring structure by introducing an equilibrium condition and taking into consideration force and momentum resultants. This approach restores the initial volume when external forces vanish and also resolves undesired heterogeneous or anisotropic artifacts caused by subdividing an object into a finite mesh structure.

An initial gallbladder model can be obtained from a 3D CT scan of a subject. The data can then be imported to the mass-spring surgical simulator. Larger shape distortions can be simulated using the gallbladder model and the simulator. The sequences of deformations can be designed to mimic endoscopic grasping or indentation of the gallbladder. Surfaces from a series of generated deformations can be used as test data.

In one example, 400 surfaces can be used for training and 100 different deformations can be used for 3D organ deformation tracking evaluation. Each 3D mesh includes 3038 vertices and a SH of degree 25 can be selected since the gallbladder surface is less complex than that of a brain.

Figure 3B:
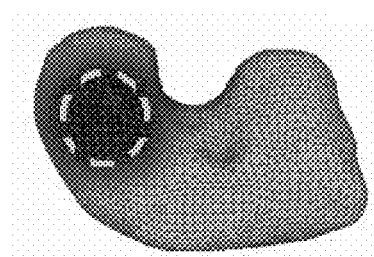
Figure 3C:
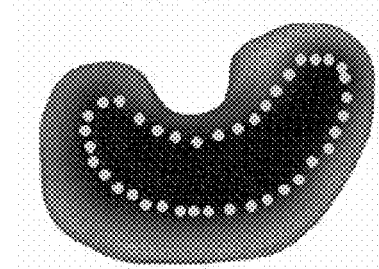

Two gallbladders were simulated and data can be stored in a memory of approximately 30 MB. FIGS. 3A, 3B, and 3C depict an organ (e.g.; a kidney) and regions for sampling. In the figures, the light grey areas indicate the locations where samples can be taken.

The global sampling strategy and the local sampling strategy (shown in FIGS. 3A and 3B, respectively) can be used to derive upper bounds on the performance of the present subject matter. The global sampling strategy uses single surface pixel uniformly distributed around the organ. The local sampling strategy uses surface patches uniformly distributed around the organ. The limited area sampling strategy (shown in FIG. 3C) corresponds to an imaging approach in which a patch of samples is acquired at a given location using a 3D optical laparoscopic or endoscopic camera with a limited view.

These sample strategies can yield well-conditioned subspace identification and spherical harmonic coefficient estimation (surface reconstruction). FIGS. 3A, 3B, and 3C illustrate global sampling, local sampling (selected optimal sampling of a localized area), and limited area sampling (restricted area where samples can be retrieved). The x, y and z coordinates of each pixel on the surface can be represented with an SH expansion and allows learning at least three subspaces per organ, at least one for each coordinate.

The SH coefficients corresponding to arbitrary deformations of the organ lie in specific lower dimensional subspaces. The low dimensionality of subspaces enables reconstruction during tracking using data from a limited view and low computational cost and training with a limited set of 3D organ image samples.

An experiment can be conducted in which 19 deformations for each of two different kidneys can be tracked using training data from two other kidneys and an initial MRI scan for the test kidney. The smallest kidney was 7 cm×4 cm×2.5 cm and the largest 9 cm×5 cm×3 cm. In this experiment, each kidney can be deformed randomly 20 times. The deformations of one kidney are not identical to that of any other kidney.

The MRI images of the training kidneys can be used to learn the subspaces in which the SH representations of the kidney surfaces can possibly lie under any deformation. The images corresponding to the test kidney are excluded from the training set and used as ground truth for evaluating the 3D organ surface tracking precision. A 3D imaging processing software can be used for segmentation of MRI slices and surface mesh rendering. Optical data can be processed using software to produce a 3D triangular mesh for the kidney portion within the scanner's field-of-view. The SH degree of the organ representation can be selected as 20, and each 3D kidney mesh can include 4002 uniformly distributed vertices. Registration of the initial MRI scan and real time optical data can be performed as described elsewhere in this document. The optical data can be acquired from less than 10% of the observable kidney side.

The error can be computed relative to the MRI data corresponding to the deformation. Across all 3D reconstructions, the average maximum tracking error, or Hausdorff distance, between the actual MRI surfaces and reconstructed 3D surfaces, was 2.10±0.32 mm with a maximum value of 2.56 mm for one test deformation on the hidden side of a kidney. The maximum error at any pixel on the observed side of the kidney across all tested kidneys and deformations was less than 1.5 mm. The average reconstruction root mean square (RMS) error is 0.70±0.07 mm with a maximum 0.8 mm.

Errors may occur in the registration step or in the use of the limited number of subspaces to capture the deformations. This error may be decreased with more training.

Characterization of the Sparse Representations and Learning Strategies

Interactions between organs in the abdomen may affect the subspaces that represent organ surface deformations. The training data set can include several deformations of a given organ or can include different examples of the organ coming from different subjects.

Training can be performed using an organ in isolation or an organ enclosed in a flexible, fixed volume surrounded by other organs. The choice of training may affect the accuracy of reconstructed deformed 3D organ surfaces.

Registration—Inter-Modality and Intra-Modality

Learning sparse surface representations may entail analysis of a set of 3D MRI or CT scans of organs from different subjects taken at different times. Combining a set of scans from different individuals taken at different times potentially with different machines and modalities requires that all points in all 3D images corresponding to the same anatomical location. Furthermore, during real time imaging, points on the 3D optical image are registered to the points produced by the SH representation corresponding to the same anatomical location.

Figure 4:
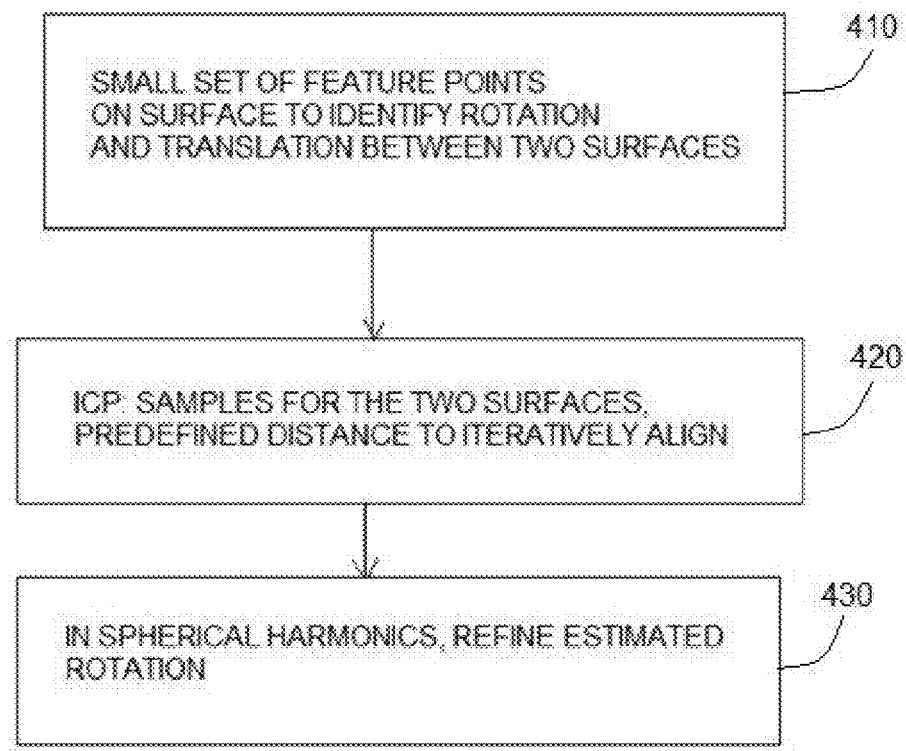
FIG. 4 illustrates surface registration during training.

Surface registration during training between different 3D images can be performed using the method shown in FIG. 4. At 410, a small set of feature points on the surface is used to identify a global rotation and translation between the two surfaces. At 420, the ICP method is implemented. In each ICP iteration, several samples are obtained from the two surfaces and sample pairs within a predefined distance are used to iteratively refine alignment. At 430, a calculation is performed in the SH domain to refine the estimated rotation between the two surfaces. The SH domain calculation is based on the fact that two points that map onto the same location after projection onto the sphere correspond to the same anatomical location.

Figure 5:
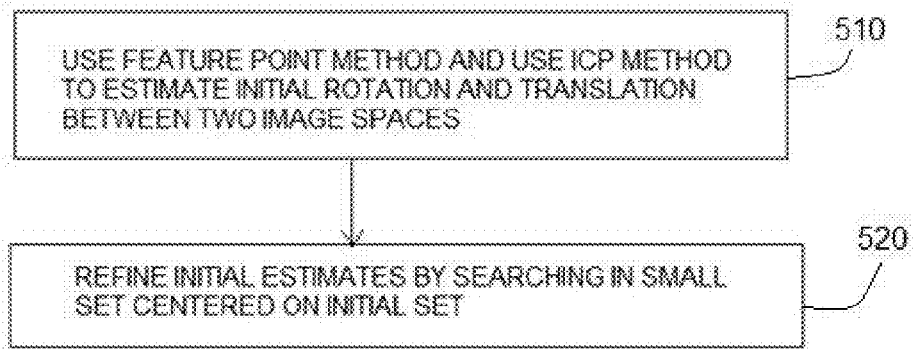
FIG. 5 illustrates registration during real time imaging.

During real time imaging, registration of the optical data to the model can be performed using a method as shown in FIG. 5. At 510, the feature point and ICP methods (described above) are used to estimate an initial rotation and translation between the two image spaces. At 520, these initial estimates are refined by searching in a small set of translations and rotations centered on the initial estimates. The search involves theorizing a specific rotation and translation, using the observed data to compute the subspace corresponding to the current surface deformation, reconstructing the surface and measuring the error between the reconstructed surface area corresponding to the observed data optical patch as determined by the theorized rotation and translation and the actual optical data patch. The choice of rotation and translation that minimizes the reconstruction error is retained as the correct estimate of translation and rotation. Registration accuracy may also be improved by using the Minimum Description Length (MDL) and covariance determinant (DetCov) registration based approach as an alternative to the SH domain rotation refinement method described above. Such methods may be more accurate than the SH based rotation refinement step and may handle surfaces that exhibit local or global rotational symmetry. In addition, an electromagnetic (EM) sensor may be coupled to the endoscope tip to track the pose of the tip and assist in the registration of the optical data with the template SH representation. The use of EM tracking information may improve image registration.

Real Time Tracking of 3D Organ Interior Structures

An example of the present subject matter includes a method for imaging arbitrary structures embedded in an organ or adipose tissue as the organ or tissue deforms during surgery. This may facilitate tactile feedback in minimally invasive surgery.

In an open surgical procedure, the surgeon may manually manipulate the organ and palpate a lesion or tumor that is not visible on the surface. With laparoscopic surgery, this may not be possible or it may not be effective with smaller or deeply seated tumors. A deep seated pancreas or liver tumor is typically not visible on the surface of the organ. Furthermore, to avoid complication during surgery, the surgeon may want to see structures, such as blood vessels, embedded in adipose tissue. A living 3D reconstructed image will move on the monitor in real time as the organ itself or adipose tissue moves and may assist the surgeon in keeping track of a tumors location in relation to the organs surface and the location of blood vessels in adipose tissue, while manipulating and exposing the organ during an operation. The surgeon can then be more accurate in deciding where to cut in order to resect the tumor.

Interior Structures and Limited Training Data

According to one example, structured sparse representations can be used to reconstruct internal and external structures in an organ. The data is derived using exterior surfaces of live samples of the organ.

According to one example, SH representations are computed for the desired interior structure and the exterior surface of the organ. Concatenations of the resulting two sets of SH coefficients fall in lower dimensional subspaces and can be used for training and reconstruction.

For training, the external surface of the organ and internal surface of the structure of interest is obtained from training using 3D MRI or CT imagery. The two sets of SH coefficients corresponding to the two surfaces can be concatenated and examined with the ISI method to uncover subspaces. The size of the training set can be selected as described elsewhere.

During reconstruction, the external optical surface samples acquired with the 3D optical camera can be used as described earlier to identify the subspace in which the concatenated SH coefficients lie, and ultimately the two sets of SH coefficients. Both surfaces can be reconstructed using the coefficients. Internal organ structures can include the chambers of a heart or internal wall of a stomach or bladder. Subspaces identified from isolated organs may differ from those identified with organs enclosed in a flexible finite volume surrounded by other organs.

A bladder model can be segmented from a 3D MRI scan. The closed surface model can be processed for artifact smoothing. The smooth surface model of the bladder can be meshed into a FE model having 26,532 tetrahedron elements and 6,669 nodes. An Elasticity Modulus of 0.05 MPa and a density of 1030 Kg/m3 can be set in the FE model as the material properties of the bladder. According to one example, 120 frames corresponding to deformations are generated using the dynamic simulation in which 90 frames are used for training and the remaining 30 frames for 3D interior surface tracking. In this example, samples taken from the exterior surface of the organ only are used to reconstruct an interior surface.

Internal Organ Surfaces Deformation

SH coefficients of the subspaces, of sufficient number and dimensions, can be used to simulate a bladder. The SH coefficients corresponding to arbitrary deformations of the external and interior walls lie in specific lower dimensional subspaces. The low dimensionality of subspaces enables accurate reconstruction of the external and internal surfaces during tracking using external samples only from a limited view and low computational cost. Reconstruction of the exterior contours may be more accurate than that of the interior contours.

For tracking tumors within an organ, tumor phantoms of different shapes and consistencies can be surgically embedded in different positions of ex vivo organs. The coarse position of the tumor is available from the pre-operative MRI or CT scan and can be used to select the proper set of subspaces before surgery if subspaces correlate with tumor position. Different tumor shapes and consistencies may lead to different subspaces. Information about the tumor shape and coarse consistency can be determined from the pre-operative scans to select the proper subspaces.

The consistency and mechanical properties of adipose tissue are differ from those of organs. Furthermore, adipose tissue lacks the features that facilitate registration between image spaces.

Part II—Sparse Representation of Deformable 3D Surface

Parametric representation of deformable object with complex surface has been a challenge in various medical applications for its demanding resource consumptions.

The present subject matter includes an algorithm to construct a compact basis for a sequence of deformed 3D surfaces, in which those surfaces can be sparsely represented with a small number of parameters. Deformed surfaces of an object can be correlated and the principle basis for representation and reconstruction can be extracted.

Organ deformation during surgical operations has been a challenging issue for various medical applications. To compensate for organ deformation, the variation of the organ shapes must be effectively represented such that the deformed surface can be rendered accordingly. However, this is not a trivial task, especially for organs with a complex surface such as the brain which contains a large amount of local details.

An example of the present subject matter includes an algorithm to achieve low-cost parametric representation of a deformable surface. By exploring the correlations among a sequence of deformed surfaces of an object, the deformed models can be sparsely represented with a small number of parameters in a space spanned by a compact basis.

An Algorithm

According to one example, an algorithm described in this section includes three components to achieve a sparse representation of a sequence of deformable 3D shapes.

First, spherical harmonics transformation (SHT) is performed to describe variable meshes in the frequency (harmonic) domain.

Second, an Orthogonal Subspace Pursuit (OSP) dictionary design method is applied to identify the subspaces that constitute the desired compact basis.

Third, calculate the sparse coefficient vector for each deformation with the obtained compact basis.

First: Spherical Harmonics Transformation

Spherical harmonics are solutions of Laplace's equation expressed in the spherical coordinates, which consists of a basis of orthogonal functions. After being properly mapped to a sphere, a genus zero 3D surface in the Cartesian coordinates with finite energy can be defined in the spherical coordinates and expanded with spherical harmonics as $$f(\theta, \varphi) = \sum_{l=0}^{\infty} \sum_{m=-l}^{+l} f_{lm} Y_{lm}(\theta, \varphi) \quad \text{(Equation II-1)}$$

where $\theta$ is the polar angle within $[0,\pi]$ and $\varphi$ is the azimuthal angel within $[0, 2\pi)$. $Y_{lm}$ is spherical harmonic of degree l and order m given explicitly as $$Y_{lm}(\theta, \varphi) = (-1)^m \sqrt{\frac{2l+1}{4\pi}} \sqrt{\frac{(l-m)!}{(l+m)!}} P_{lm}(\cos\theta) e^{im\varphi} \quad \text{(Equation II-2)}$$

where $P_{lm}$ is the associated Legendre polynomial of order m. The harmonic coefficients $f_{lm}$ is approximated using the inner product of the function $f(\theta,\varphi)$ and the basis $Y_{lm}(\theta,\varphi)$:

$$f_{lm} = <f(\theta, \varphi), Y_{lm}(\theta, \varphi)> \quad \text{(Equation II-3)}$$
$$= \int_{\varphi=0}^{2\pi} \int_{\theta=0}^{\pi} f(\theta, \varphi) Y_{lm}(\theta, \varphi) \sin\theta d\varphi d\theta$$

The summation in Equation II-1 is truncated by limiting l up to a number L to approximate $f(\theta,\varphi)$. Let Y denote the matrix composed of $(L+1)^2$ harmonics sampled at N points on the surface, then Y has the following formation $$Y = |\vec{Y}_{0,0} \vec{Y}_{1,-1} \ldots \vec{Y}_{L,L}|_{N \times (L+1)^2} \quad \text{(Equation II-4)}$$

in which, $\vec{Y}_{lm}$ is a vector with N elements corresponding to samples $(\theta_i, \varphi_i)_{i=1}^N$. Then Equation II-1 can be expressed as $$f = Y\vec{f} \quad \text{(Equation II-5)}$$

where f stands for $f(\theta,\varphi)$ and $\vec{f} = [f_{0,0}\ f_{1,-1}\ \ldots\ f_{L,L}]^T$ is the harmonic coefficient vector. The linear system is solved with the least square (LS) constraints outputting $\vec{f}$ $$\vec{f} = (Y^T Y)^{-1} Y^T f \quad \text{(Equation II-6)}$$

The computation complexity for solving Equation II-6 can be alleviated by employing an iterative residual fitting (IRF) algorithm. For a sequence of K deformed surfaces, let the kth surface be represented by $\vec{f}_k$, then the group of deformations can be described by matrix F:

$$F = |\vec{f}_1\ \vec{f}_2 \ldots \vec{f}_K|_{(L+1)^2 \times K} \quad \text{(Equation II-7)}$$

Second: Subspace Pursuit Decomposition

Subspace Pursuit Decomposition explores the correlations among those deformations based on the coefficient matrix F derived in the first step. An OSP decomposition is used first to identify the subspaces where each vector in F lives for constructing a compact dictionary D. Then all the vectors living in the same subspace are clustered and their corresponding coefficients are calculated.

The OSP subspace searching is an iterative process which terminates when a pre-defined criteria is met. The detailed description of the OSP algorithm is given in B. V. Gowreesunker and A. H. Tewfik, "A Novel Subspace Clustering Method for Dictionary Design", ICA 2009, (incorporated herein by reference). In one example of the present subject matter, the stopping criteria includes two components: 1) an error threshold $\varepsilon$ for subspaces detection; and 2) a maximum number of iterations $E_{max}$ for avoiding deadlock searching.

Once a subspace $A_i$ spanned by $n_i$ basis is determined, a vector $\vec{f}_k$ in F is selected if the normalized Euclidean distance between itself and its projection in $A_i$ is less than a given threshold $\eta$. Its corresponding coefficients $\vec{c}_k$ for the $n_i$ basis is calculated using LS estimation. Now $\vec{f}_k$ can be approximated with $$\vec{f}_k = A_i \vec{c}_k \quad \text{(Equation II-8)}$$

If there exists J subspaces in which the $\{\vec{f}_k\}_{k=1}^K$ are clustered, the final dictionary D is constructed as the union of all the subspaces: $D = U_{i=1}^J \{A_i\}$. The coefficients $\{\vec{c}_k\}_{k=1}^K$ with length $n_i$ (the number of basis in subspace $A_i$) is extended to $\{\tilde{\vec{c}}_k\}_{k=1}^K$ with length $I = \Sigma_{i=1}^J n_i$ (the total number of base vectors in D) by inserting zeroes in positions corresponding to other subspaces. For instance, if $\vec{f}_1$ lies in subspace $A_2$ which are spanned by column 2 and 3 in D, then $\{\tilde{\vec{c}}_k\}$ has nonzero values only at index of 2 and 3. Consequently, F can be approximated as $$\hat{F} = |\hat{\vec{f}}_1\ \hat{\vec{f}}_2\ \ldots\ \hat{\vec{f}}_K|_{(L+1)^2 \times K} \quad \text{(Equation II-9)}$$
$$= DC$$

where $D = U_{i=1}^J \{A_i\}$ is a $(L+1)^2 \times I$ matrix and $$C = |\tilde{\vec{c}}_1\ \tilde{\vec{c}}_2 \ldots \tilde{\vec{c}}_K|_{I \times K} \quad \text{(Equation II-10)}$$

I usually is substantially smaller than both K and $(L+1)^2$, the benefit of which will be further discussed in a later section.

To summarize, the decomposition process includes the following procedures:
1. Initialization: $i=0$, $D=\emptyset$, $F^0=F$,
2. Subspace searching and clustering
  (i) $i=i+1$; choose the ith vector $\vec{f}_i$ and let $F^i = F^{i-1} \otimes \vec{f}_i$.
  (ii) Find $n_i$ vectors from $F^i$ to form $S_i$ with OSP for representing $\vec{f}$ with error no larger than $\varepsilon$ within $E_{max}$ iterations; if failed, let $A_i = \vec{f}$ and jump to step (vi).
  (iii) Perform SVD decomposition on $S_i$: $U\Sigma V^T = S_i$; Let $A_i$ contain the first $n_i$ vectors of U.
  (iv) Select vectors from F that can be represented by $A_i$ with error distance bounded by $\eta$, and then remove them from $F^i$.
  (v) Calculate coefficient $\vec{c}_k$ and build $\tilde{\vec{c}}_k$
  (vi) Repeat subspace searching and clustering until all the vectors are clustered.
3. Form matrix $D = U_{i=1}^J A_i$ and C according to Equation II-10 to get $\hat{F}$ in Equation II-9.

Three: Sparse Surface Representation

Combining the results from the SHT and the subspace pursuit decomposition, a sequence of deformations $\{f_k\}_{k=1}^K$ can be approximately represented by a sparse matrix C derived by integrating Equation II-5, Equation II-7 and Equation II-9:

$$|\hat{f}_1\ \hat{f}_2\ \ldots\ \hat{f}_K|_{N \times K} = YDC = GC \quad \text{(Equation II-11)}$$

where G=YD is the overall basis with the size of N×I. Once computed, the system stores two matrix G and C with dimensions N×I and I×K, respectively.

In traditional SH based methods, $\{f_k\}_{k=1}^K$ is approximated with $$|\hat{f}_1 \hat{f}_2 \ldots \hat{f}_K|_{N \times K} = YF \quad \text{(Equation II-12)}$$

where Y and F have dimensions of $N \times (L+1)^2$ and $(L+1)^2 \times K$, respectively.

Comparing the above two methods, during each deformed surface reconstruction (G, C, Y, F are all known), Equation II-11 is much less costly than Equation II-12 in terms of both computation time and memory space. Specifically, in Equation II-11, GC requires $I \times (N+K)$ units of memory with $N \times I \times K$ multiplications; while Equation II-12 needs $(L+1)^2 \times (N+K)$ units of memory with $N \times (L+1)^2 \times K$ multiplications. Note that $I \ll (L+1)^2$.

Triangular brain mesh data can be used as the initial model. Software such as SOFA (Simulation Open Framework Architecture) can be used for generating a sequence of (K=35) deformations. The simulation is conducted using a program executing on a processor (1.2 GHz, 1 GB memory). Each 3D brain mesh includes N=40962 points and is approximated using spherical harmonics up to degree L=80.

The 35 deformed surfaces can be quickly reconstructed in the level of milliseconds with Equation II-11.

The present subject matter includes an algorithm for parametric representation of deformable objects. In this example, a sequence of deformed surfaces of an organ can be represented with a compact basis and sparse coefficient vectors. The present subject matter explores the underlying correlations among deformed surfaces. An example of the present subject matter can be used for sparse representations of deformable surfaces pursuant to various applications, such as shape analysis and classification, 3D mesh compression and shape database construction.

Part III—In Vivo Tracking Using Spherical Harmonics and Subspace Clustering

Deformable organ tracking has been a challenge in various medical applications. An example of the present subject matter includes an algorithm for 3D organ tracking based on spherical harmonics (SH) and subspace clustering. The potential deformation subspaces are identified from training data, based on which an extremely low density sampling strategy and a low cost deformation construction method are designed. The present subject matter can be applied to in vivo 3D organ tracking and visualization during surgical intervention.

Natural organ deformation during operations has imposed substantial challenges on physicians and surgeons in various medical applications. Taking stereotactic body radiosurgery for instance, the uncertainty resulting from respiratory motion usually leads to overestimated dose delivery. Moreover, real time tracking and visualization of organ deformation is one of the major obstacles to facilitate the progress of the emerging surgical approach of NOTES during which surgeons inflate the abdomen to gain a better working space.

Organ deformation is constrained by some physical limitations such as tissue rigidity and surrounding boundary. Accordingly, a space identified out of a thorough set of training information embraces all the possible deformations of that organ. An example of the present subject matter identifies the potential deformation space and includes designs for an efficient sampling strategy and deformed surface construction.

An Algorithm

An algorithm according to the present subject matter includes three components.

First, subspaces in which the deformed surfaces can be linearly represented with a few coefficients are identified using spherical harmonic transform (SHT) and subspace pursuit.

Second, a sampling strategy is designed to determine appropriate sampling positions for deformation tracking.

Third, the deformed surface is reconstructed efficiently.
First: Basic Space Identification A sequence of training deformation data is plugged into this initial step to find all the basis that span the deformation subspaces through the following three procedures.
Spherical Harmonic Transform SHT can be used for genus zero 3D surface representation. After being properly mapped to a sphere, a surface $x_k(\theta,\varphi)$ ($1 \leq k \leq K$ in the training sequence) can be defined in the spherical coordinates and expanded with orthogonal spherical harmonics as $$x_k(\theta, \varphi) = \sum_{l=0}^{\infty} \sum_{m=-l}^{+l} f_{lmk} Y_{lm}(\theta, \varphi) \quad \text{(Equation III-1)}$$

where $\theta$ and $\varphi$ are the polar and azimuthal angles within $[0,\pi]$ and $[0,2\pi]$, respectively. $Y_{lm}$ is SH of degree l and order m. The harmonic coefficients $f_{lmk}$ is approximated using the inner product of the function $x_k(\theta,\varphi)$ and the basis $Y_{lm}(\theta,\varphi)$. The summation in Equation III-1 is truncated by limiting l up to a number L for approximation. Let Y denote the matrix composed of $(L+1)^2$ harmonics sampled at N points on the surface. Y has the following formation $$Y = |\vec{Y}_{0,0} \ \vec{Y}_{1,-1} \ldots \ \vec{Y}_{L,L}|_{N \times (L+1)^2} \quad \text{(Equation III-2)}$$

in which $\vec{Y}_{lm}$ is a vector with N elements corresponding to samples at $(\theta_i,\varphi_i)_{i=1}^N$. Then Equation III-1 can be expressed as $$\vec{x}_k = Y \vec{f}_k \quad \text{(Equation III-3)}$$

where $\vec{x}_k$ and $\vec{f}_k$ are the vector format of $x_k(\theta,\varphi)$ and its corresponding harmonic coefficients. The linear system is solved with the least square (LS) constraints generating $\vec{f}_k$.

$$\vec{f}_k = (Y^T Y)^{-1} Y^T \vec{x}_k \quad \text{(Equation III-4)}$$

For a sequence of K training surfaces, the group of deformations can be approximated as:

$$\hat{X} = YF \quad \text{(Equation III-5)}$$

where $\hat{X}$ includes an estimated $\{\vec{\hat{c}}_k\}_{k=1}^K$ and F includes $\{\vec{f}_k\}_{k=1}^K$. Thus the entire training set is characterized by F which is further explored in the following sections.
Subspace Pursuit and Vector Clustering This procedure is to pursuit all the subspaces embedded in vectors $\{\vec{f}_k\}_{k=1}^K$ for clustering. Briefly, the pursuit approach includes the following:

Initially, the $J (J \geq 1)$ subspaces $\{U_i\}_{i=1}^J$ are identified from F via the OSP decomposition. Each subspace is spanned by $n_i$ vectors. $I = \Sigma_{i=1}^J n_i$ is the total number of vectors in all the subspaces. A base matrix D is built as the union of all the subspaces: $D = U_{i=1}^J \{U_i\}$ with size of $(L+1)^2 \times I$. Then all the vectors of matrix F are clustered into those subspaces $U_i$ and the coefficients $\vec{p}_k$ are calculated accordingly using LS approximation. Therefore, each $\vec{f}_k$ can be expressed as:

$$\vec{f}_k = U_i \vec{p}_k \quad \text{(Equation III-6)}$$

Extend $\vec{p}_k$ to a $\tilde{\vec{p}}_k$ by padding zeros at the positions corresponding to other subspaces, generating a sparse coefficient matrix $P=|\vec{p}_1\ \vec{p}_2\ \ldots\ \vec{p}_K|_{J \times K}$. Then F can be expressed as $$F = |\vec{f}_1\ \vec{f}_2\ \cdots\ \vec{f}_K|_{(L+1)^2 \times K} \quad \text{(Equation III-7)}$$
$$= DP$$

Sparse Surface Representation

Based on the previous SHT process along with subspace pursuit and vector clustering, a combination of Equation III-5 and Equation III-7 yields a derivation for the following formulation for approximating the training sequence of deformations:

$$\hat{X} = YDP = GP \quad \text{(Equation III-8)}$$

Where G=YD with size of N×I. Since $D=U_{i=1}^{J}\{U_i\}$, G can be expressed $G=U_{i=1}^{J}\{G_i\}$ with $G_i=YU_i$. Then each deformation (e.g., living in subspace $G_i$) can be estimated as $$\hat{\vec{x}}_k = G\tilde{\vec{p}}_k = G_i\vec{p}_k \quad \text{(Equation III-9)}$$

The identified matrix G contains J desired subspaces $G_i$, each of which spans one potential deformation subspace. At this point, each deformation $\vec{x}_k$ can be approximated in terms of vectors in G with sparse coefficient vector $\tilde{\vec{p}}_k$ in matrix P. This compact formulation and orthogonal subspace basis $G_i$ enables the following sampling strategy design and surface construction.

Two: Sampling Strategy Design

With the obtained G from the previous processing, the sampling strategy design entails selecting a few sampling positions suitable to track the change of the organ, such that the deformation can be constructed based on those points.

Considering the orthogonality among columns in $G_i$, the computation accuracy involving $G_i$ is guaranteed for its small condition number. However this does not necessarily hold for the combined matrix G, since intersections may exist among those subspaces. Therefore, the sampling positions are selected for each subspace $G_i$ and then samples are taken from all those chosen positions on the organ under tracking.

Denote $\vec{h}_j$ as the surface to be constructed and $\tilde{\vec{h}}_j$ as the samples to be chosen. Let $\tilde{G}_i$ stand for the sub-matrix containing $m_i$ ($m_i$ is slightly larger than $n_i$) rows of $G_i$. The philosophy behind the sampling position design is to find a well conditioned sub-matrix $\tilde{G}_i$, such that the coefficient vector $\vec{p}_j$ can be stably estimated conforming to the LS constraint.

Since the basis in $G_i$ are orthogonal, the likelihood of getting a $\tilde{G}_i$ with small condition number are high. Finding the $\tilde{G}_i$ with the smallest condition number is optimal in terms of computation accuracy. However its complexity grows exponentially with the scale of the matrix for exhausting all the possible $\tilde{G}_i$s. A compromised way is a "random walk" searching: randomly pick $m_i$ rows from $G_i$ to form $\tilde{G}_i$ for a predefined number of iterations (e.g., 1000 times in one example simulation), and choose the $\tilde{G}_i$ with the smallest condition number. The index set of the chosen rows is recorded as $S_i = \{s_{i,1}, s_{i,2}, \ldots s_{i,m_i}\}$.

Having determined $S_i$, the indices in $S_i$ are applied as the desired sampling positions for subspace $G_i$. In such a way, the overall sampling strategy is designed as $S = U_{i=1}^{J}\{S_i\}$. The samples taken for subspace $G_i$ can be denoted as a vector $\tilde{\vec{h}}_{j,i} = [h_j(s_{i,1}) \ldots h_j(s_{i,m_i})]$. Then the total sample vector is $\tilde{\vec{h}}_j = U_{i=1}^{J}\{\tilde{\vec{h}}_{j,i}\}$ with length $M = \Sigma_{i=1}^{J} m_i$.

Note that M can be two or three-order magnitude smaller than the initial number of surface samples N. This low sampling density reduces the computation cost.

Three: Deformation Construction

This step includes determining which subspace the deformation best fits in and construct the whole surface in this subspace with the samples taken from the previous step.

For J subspaces, there are J optional estimations for coefficient vector $\vec{p}_j$ to construct the organ surface with Equation III-9. Based on LS constraint, the estimations are formulated as $$\hat{\vec{p}}_{j,i} = (\tilde{G}_i^T \tilde{G}_i)^{-1} \tilde{G}_i^T \tilde{\vec{h}}_{j,i} \quad (1 \leq i \leq J) \quad \text{(Equation III-10)}$$

The construction error at sampling points $S_i$ for each subspace is used as the parameter for deciding the optimal subspace $G_i$ to which the current deformation $\vec{h}_j$ belongs. Corresponding coefficient vector is denoted as $\hat{\vec{p}}_{j,i^*}$, where $i^*$ is determined by minimizing the Euclidean distance $$i^* = \min_{1 \leq i \leq J}\left(\left\|\tilde{\vec{h}}_{j,i} - \tilde{G}_i \hat{\vec{p}}_{j,i}\right\|_2\right) \quad \text{(Equation III-11)}$$

According to Equation III-9 and Equation III-10, the deformed surface can be constructed as $$\hat{\vec{h}}_j = G_{i^*}\hat{\vec{p}}_{j,i^*} = G_{i^*}(\tilde{G}_{i^*}^T \tilde{G}_{i^*})^{-1} \tilde{G}_{i^*}^T \tilde{\vec{h}}_{j,i^*} \quad \text{(Equation III-12)}$$

For comparison, the traditional SH construction approach is implemented via Equation III-3 and Equation III-4, such that $$\hat{\vec{h}}_j = Y(Y^T Y)^{-1} Y^T \vec{h}_j \quad \text{(Equation III-13)}$$

Considering the matrix Y with size $N \times (L+1)^2$, where N and $(L+1)^2$ are large numbers for organ with complicated surface, e.g., N>40000 and L>70 for the cortical surface. The traditional SH construction method (Equation III-13) results in undesired computational bottleneck; while the method in Equation III-12 is exempted from the resource burden for the small matrix size of $G_i(N \times n_i)$ and $\tilde{G}_i(m_i \times n_i)$, where $R = \max(n_i, m_i) \ll N$, $(L+1)^2$ as shown elsewhere in this document.

The matrix inverse calculation $(\tilde{G}_i^T \tilde{G}_i)^{-1}$ in Equation III-12 needs $O(n_i^2 R)$ multiplications as opposed to $O(L^3)$ in Equation III-13. Moreover, the reduction of sample size from N to M eases the matrix multiplication and memory occupation.

Evaluation

An algorithm using 3D cortical mesh data can be evaluated. The deformation is generated with software. There are K=35 deformations during training stage and 30 new deformations for tracking process. Simulation is run on a processor (1.2 GHz) with 1 GB memory. Each brain mesh consists of N=40962 points and SH up to degree L=80 were applied for approximation.

Based on the training deformations, subspaces on X, Y and Z axis are identified respectively.

After the deformation subspaces being identified, only M=29 sample positions need to be monitored for the brain surface tracking and reconstruction. The overall memory storing subspace matrices is only 9 MB and each deformed surface can be reconstructed in milliseconds with the present algorithm.

An example of the present subject matter includes an algorithm for 3D organ tracking using SH and subspace clustering. By identifying the deformation subspaces through training data, deformed organ surfaces can be constructed on real time with low sampling density while maintaining high accuracy. The method can be directly applied to in vivo organ tracking in NOTES using minimal sampling locations

Part IV—Tracking of Exterior and Interior Organ Surfaces

The present subject matter includes an algorithm for real time tracking of the exterior and interior surfaces of organs using sparse sampling of the exterior surfaces. Tracking is based on identifying subspaces in which the coefficients of spherical harmonic representations of the surfaces live. The present subject matter uses pre-operative CT/MRI scans during training, and needlescopic images (or endoscope images or laparoscope images) acquired during tracking.

Various strategies can be implemented for sampling the exterior organ surface using the images and also apply the method to 3D frame interpolation.

An example of the present subject matter includes a method for tracking interior unobservable surfaces from the exterior observable images. Various sampling strategies are presented to achieve real time tracking with limited field-of-view.

According to one example, the tracking method uses preoperative CT or MRI scans for training and then acquires samples from fiber optic needlescopic cameras (or an endoscope camera or other camera) during surgery for deformation rendering.

An example algorithm includes three elements: first, subspaces in which the deformed surfaces can be efficiently represented are identified; second, three sparse sampling strategies are designed to track the interior and exterior deformation using samples from exterior only; and third, the deformed surface is reconstructed in the best-fit subspace using selected samples.

First: Subspace Identification and Efficient Surface Representation

A large set of 3D training deformations obtained from preoperative CT/MRI images are generated to identify the deformation subspaces in which each deformation can be represented with a low dimension vector.

Spherical Harmonic Transform (SHT)

For an organ including both interior and exterior surface, individual parameterization is conducted for both sides. Denote $\hat{x}_k^{in}$ and $\vec{x}_k^{ex}$ ($1 \leq k \leq K$) as the interior and exterior surface in the training frames, respectively. Then each pair of $\vec{x}_k^{in}$ (with $N_1$ vertices) and $\vec{x}_k^{ex}$ (with $N_2$ vertices) can be approximated by SH basis in a matrix format as $$\begin{bmatrix} \vec{\hat{x}}_k^{in} \\ \vec{\hat{x}}_k^{ex} \end{bmatrix} = \begin{bmatrix} Y^{in} & 0 \\ 0 & Y^{ex} \end{bmatrix} \cdot \begin{bmatrix} \vec{f}_k^{in} \\ \vec{f}_k^{ex} \end{bmatrix} \quad \text{(Equation IV-1)}$$

where $Y^{in}$ of size $N_1 \times (L+1)^2$ and $Y^{ex}$ of size $N_2 \times (L+1)^2$ denote the SH basis matrix for interior and exterior respectively, each of which consists of discrete harmonics up to level L. $\vec{f}_k^{in}$ and $\vec{f}_k^{ex}$ are the corresponding harmonic coefficient vectors. Therefore, each deformation can be represented by vector $$\vec{f}_k = \begin{bmatrix} \vec{f}_k^{in} \\ \vec{f}_k^{ex} \end{bmatrix},$$

and all K training frames can be characterized by $F = U\{\vec{f}_k\}_{k=1}^K$.

Subspace Pursuit and Vector Clustering

Initially, $J(J \geq 1)$ subspaces $\{U_i\}_{i=1}^J$ are identified from vectors $\{\vec{f}_k\}_{k=1}^K$ via OSP. Each subspace is spanned by $n_i$ vectors. Then all vectors of matrix F are clustered into those subspaces $U_i$ and the coefficients $\vec{p}_k$ are calculated accordingly using LS approximation. So, each $\vec{f}_k$ can be approximated in its subspace as:

$$\vec{f}_k = U_i \vec{p}_k \quad \text{(Equation IV-2)}$$

Efficient Surface Representation

Based on the previous SHT process along with subspace pursuit and vector clustering, combining Equation IV-1 and Equation IV-2, enables representing each training deformation as:

$$\begin{bmatrix} \vec{\hat{x}}_k^{in} \\ \vec{\hat{x}}_k^{ex} \end{bmatrix} = \begin{bmatrix} Y^{in} & 0 \\ 0 & Y^{ex} \end{bmatrix} U_i \vec{p}_k = G_i \vec{p}_k \quad \text{(Equation IV-3)}$$

where $$G_i = \begin{bmatrix} Y^{in} & 0 \\ 0 & Y^{ex} \end{bmatrix} U_i$$

with size of $(N_1+N_2) \times n_i$.

Equation IV-3 indicates that each deformation can be approximated with a low dimension coefficient vector $\vec{p}_k$ in $G_i$. This compact representation and orthogonality of subspace $G_i$ enables the following efficient sampling strategy design and surface construction.

Two: Sampling Strategy Design

With obtained matrix $G_i$, the sampling strategy design aims to determine the sampling locations on the exterior to reconstruct the deformation on both interior and exterior. The samples can be obtained through a fiber optic camera with a rotating off-axis aperture or sparse time sampling of CT scans. Three sampling strategies are introduced in the following section: completely random sampling, patch sampling and localized sampling.

Random Sampling

Denote $$\vec{h} = \begin{bmatrix} \vec{h}^{in} \\ \vec{h}^{ex} \end{bmatrix}$$

as the deformed surface to be constructed and subset $\tilde{\vec{h}}^{ex}$ as the $m_i$ samples to be chosen from the exterior. Let $\tilde{G}_i$ stands for the sub-matrix containing $m_i$ ($n_i<m_i\ll N_2$) rows of $G_i$. The philosophy behind the sampling design is to find an index set $S_i=\{s_{i,l}|1\leq l\leq m_i\}$ with each atom within $\{N_1+1$ $N_1+N_2]$ to form a well conditioned sub-matrix $\tilde{G}_i$ and corresponding sample set $\tilde{\vec{h}}^{ex}$, such that the over-determined linear system $$\tilde{\vec{h}}^{ex}=\tilde{G}_i\vec{p}_i \text{ for } i=1\ldots J \quad \text{(Equation IV-4)}$$

can be well solved under LS constraints for coefficient vector $\vec{p}_i$ in each subspace $G_i$. Then the subspace with the least error at the known samples is chosen as the best-fit subspace for reconstructing the overall surface $\bar{h}$.

Since the computational complexity of finding $\tilde{G}_i$ with the smallest condition number grows exponentially with the scale of the matrix, a "random walk" searching is adopted for simplicity: randomly pick $m_i$ out of the lower $N_2$ rows from $G_i$ to form $\tilde{G}_i$ for a predefined number of trials (e.g., 1000 times in our simulation), and choose $S_i$ as the index set which constructs $\tilde{G}_i$ with the smallest condition number. Then atoms in $S_i$ are used as the desired sampling positions, that is, the sample set in subspace $G_i$ can be formulated as $\vec{h}_i^{ex}=[h(s_{i,1})\ldots h(s_{i,m_i})]$. Notice that each $s_{i,l}$ is in the range of $[N_1+1 \ N_1+N_2]$, so every selected sampling position must locate on the exterior.

Sampling with Localization

In situations where only a few observation instruments (such as fiber optics) are available or the view of the exterior surface of the organ is limited, completely random sampling may be difficult to implement. To reduce the overall monitoring area, certain sampling localization constraints can be introduced while determining index set Si for each subspace.

1. Random Patch Sampling

In this sampling mode, all the surface vertices are initially grouped into patches of size $n(n<m_i)$ which can be taken using a single fiber optic camera. Each patch contains n nearest neighbors without overlapping among patches. Thus, there are $R=\lfloor N/n\rfloor$ patches, and $\lfloor a\rfloor$ stands for the integer that is closest to but smaller than a. The number of patches to be chosen is $r=\lceil m_i/n\rceil$ with $\lceil a\rceil$ as the smallest integer that is larger than a. To seek a well-conditioned $\tilde{G}_i$, randomly select r out of R patches for a predefined times and choose the r patches whose index generates $\tilde{G}_i$ with smallest condition number.

2. Localized Sampling

This strategy represents a combination of completely random sampling and patch sampling, which takes random samples from one concentrated area. Similar to patch sampling, surface vertices are grouped into patches of size n and $R=\lfloor N/n\rfloor$, but n is at least 3 times larger than $m_i$. Within each patch, run the same "random walk" searching process and record the resulted index set as $S_{i,q}$ ($1\leq q\leq R$). After exhausting all the patches, the index set $S_{i,p}$ leading to the best-conditioned $\tilde{G}_i$ is chosen as the desired sampling location $S_i$ for that subspace and the corresponding patch is the localized area monitored by a few fiber cameras.

Three: Deformation Construction

Next, decide which subspace the deformation best fits in and construct the whole surface using the samples taken from the previous step.

For J subspaces, each coefficient vector $\vec{p}_i$ ($1\leq i\leq J$) can be estimated as:

$$\hat{\vec{p}}_i=(\tilde{G}_i^T\tilde{G}_i)^{-1}\tilde{G}_i^T\tilde{\vec{h}}_i \ (1\leq i\leq J) \quad \text{(Equation IV-5)}$$

The construction error at sampling points for each subspace is used as the parameter for deciding the optimal subspace $G_{i^*}$ to which the current deformation $\vec{h}$ belongs. That is, $i^*=\min_{1\leq i\leq J}(\|\tilde{\vec{h}}_i-\tilde{G}_i\hat{\vec{p}}_i\|_2)$. Then the overall surface can be reconstructed as $\vec{h}=G_{i^*}\hat{\vec{p}}_{i^*}$.

Compared with compressed sensing MRI conducted in Fourier domain, the proposed strategy uses samples in the spatial domain. Furthermore, it specially exploits subspaces rather than the sparseness of a representation of the object in an particular domain (e.g. wavelet), which enables the block sparse sampling strategy. As shown, one example includes sparse sampling in both deformation tracking and 3D frame interpolation.

An initial finite element volume model of a bladder including interior and exterior walls is deformed to mimic its interaction with an instrument. The surface mesh of each deformed volumetric bladder is extracted as testing data. Simulation is run using a processor having 2 GB memory. The bladder model has $N_1=4434$ and $N_2=4274$ vertices in the interior and exterior, respectively. SH level L is set to be 30. K=90 frames are used for training and 30 different frames are tested for tracking.

Three sampling strategies can be evaluated for tracking, including random sampling, patch sampling and localized sampling on the exterior of the bladder surface.

The present subject matter for tracking interior deformation using samples from exterior can be applied to 3D surface sequence interpolation. This is achieved by treating every two consecutive deformations as interior and exterior of a whole objet, and then following the same training and sampling design as described elsewhere. Therefore the second ("interior") deformation can be completely estimated with samples from the first ("exterior") deformation.

In one example, 2D CT images are reconstructed. The resulted 3D triangular meshes are further re-sampled and remeshed. According to one example, a method includes: (1) construct an icosahedron of M vertices (e.g., M=4002) with radius large enough to embrace the largest heart volume among the sequence; (2) move the center of the 3D surfaces to the origin of icosahedron; (3) for each segment originated from the origin point to every different vertex on the icosahedron, find the triangle on the heart mesh that intersects with the segment; (4) calculate the intersection point accordingly and use it as the new surface point. The "star-like" shape of a heart yields one and only one intersection between each line segment and the surface.

Interpolation

In this example, 10 of the 11 phases are randomly chosen for training, and the remaining one are used for testing the performance of phase interpolation. The SH level L is set to be 10 and patch sampling strategy is applied.

With 45 samples from 3 patches located in the first ("exterior") deformation, the average interpolation error for the testing frame acceptably low. The interpolation method yields high accuracy. Since only 12% (45/4002) of the heart surface needs to be imaged to construct the current and the following frames, an example of the present subject matter is able to reduce the number of CT images to less than 10% of the number acquired in the traditional routine.

An example of the present subject matter includes a method for tracking 3D deformations in both interior and exterior surfaces of an organ with sparse samples taken from the exterior surfaces only. Using 5-10 needlescopic fiber cameras can provides real time tracking. Thus, this low sampling density enables its application in minimum invasive surgery when only limited visual access to the organ is available. Meanwhile, it can be directly applied in 3D temporal interpolation in dynamic function analysis to reduce the CT/MRI radiation suffered by the patients.

Figure 6:
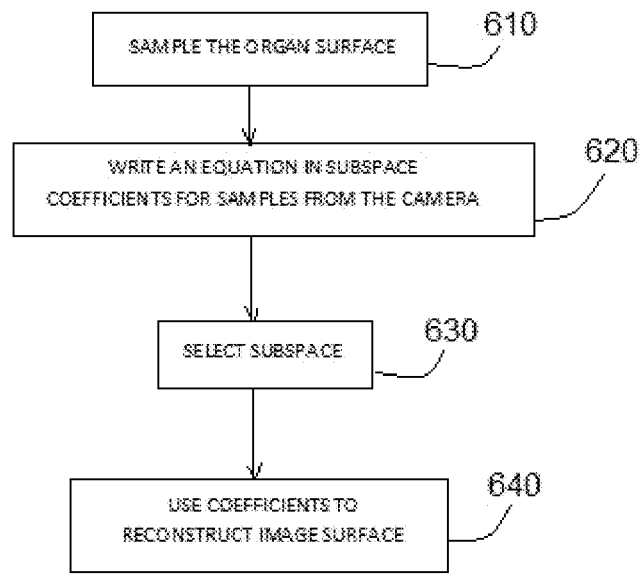
FIG. 6 illustrates surface reconstruction according to one example.

FIG. 6 illustrates an example of a method for reconstructing an image of an object using the present subject matter. The figure can be interpreted to allow imaging of an external surface of the object, an internal surface of the object or both internal and external surfaces of the object. As noted earlier, the object can include an organ or other 3D object.

At 610, the organ surface is sampled. Sampling can include generating data using an MRI modality, a CT scan, an ultrasound, a video camera or other system. Sampling can occur during the training process as well as during the reconstruction process. Consider an example in which the object is undergoing reconstruction. As such, sampling may include a single MRI image (at a pre-operative stage) followed by sampling using an optical probe (or camera) of an endoscopic instrument. In particular, a plurality of visible locations on the surface of the object can be sampled using such a probe. The locations and distribution of the object surface can be determined as described elsewhere in this document. As a result of the sampling, at 630, equations having subspace coefficients are generated using samples from the camera. At 630, a subspace is selected. Various algorithms are described herein for selecting a subspace. At 640, the coefficients are used to generate an image of the surface.

Figure 7:
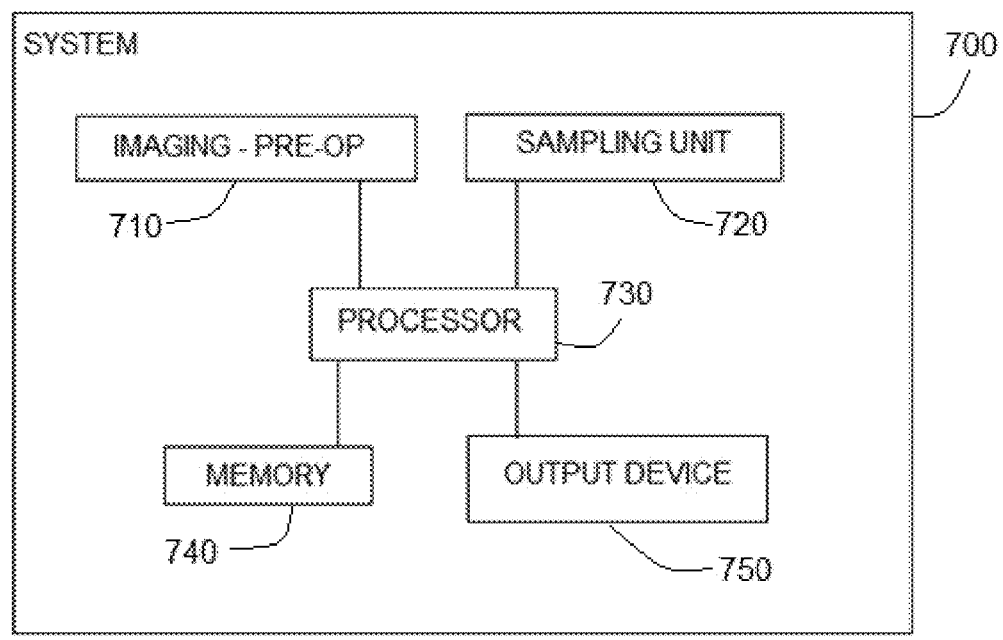
FIG. 7 illustrates a system according to one example.

FIG. 7 illustrates system 700 according to one example. System 700 includes an imaging module 710. Imaging module 710 can include an MRI system, a CT scanner, an ultrasound imaging or other apparatus configured to generate an image prior to a surgical procedure. Imaging module 710 is communicatively coupled to processor 730. Processor 730 can include a computer (personal computer, laptop, server, or other signal processor. In one example, processor 730 is coupled to imaging module 710 as well as other components of system 700 by a wired or wireless communication link. Sampling unit 720 is coupled to processor 730. Sampling unit 720 can include an endoscope, a needlescope, a camera, or other instrument to collect sample measurements of a surface of an object (or organ). Memory 740 and output device 750 are also coupled to processor 730. In various examples, memory 740 provides storage for data and executable instructions for implementation by processor 730. In one example, memory 740 includes a computer readable medium for storage of instructions. Output device 750 can include a display screen, a monitor, a storage device, a printer, a memory device, or other apparatus for producing a representation of the object.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A method comprising:
   receiving data corresponding to a sequence of deformations of a deformable object;
   transforming the data to an expression in spherical harmonics;
   using the expression in spherical harmonics to perform a decomposition;
   selecting a plurality of sample positions for the object and receiving object data for the sample positions; and
   using a processor to generate a reconstruction of the object based on the object data and based on coefficients determined by the decomposition.

2. The method of claim 1 wherein receiving data includes receiving data from an in vivo organ.

3. The method of claim 1 wherein transforming the data to an expression in spherical harmonics includes calculating a matrix having coefficients corresponding to the deformation.

4. The method of claim 1 wherein using the expression in spherical harmonics to perform a decomposition includes identify a correlation between deformations in the sequence.

5. A system comprising:
   an imaging module configured to receive image data corresponding to a pre-operative image of an organ, the organ having a deformable surface and the image data including at least one of ultrasound image data, computerized tomography data, or magnetic resonance data;
   a memory configured to store training data corresponding to the organ, the training data including spherical harmonic representations of a plurality of deformations of the organ;
   a sampling unit configured to receive sample measurements of an exterior surface of the organ, the sample measurements corresponding to a subset of the exterior surface;
   a processor configured to receive the image data and receive the sample measurements and generate a reconstructed image of the organ based on a spherical harmonics transformation and based on the training data; and
   an output device configured to display the reconstructed image.

6. The system of claim 5 wherein the processor is configured to generate the reconstructed image having an interior surface.

7. The system of claim 5 wherein the sampling unit includes at least one of an endoscope and a laparoscope.

8. The system of claim 5 wherein the processor is configured to perform a decomposition of the spherical harmonic representations, wherein the decomposition includes executing an algorithm implementing subspace pursuit and clustering.

9. The system of claim 5 wherein the reconstructed image includes the exterior surface and wherein the subset of the surface is approximately 10% of the exterior surface.

10. The system of claim 5 wherein the processor is configured to generate real time data corresponding to the reconstructed image.

11. A system comprising:
    a processor configured to receive pre-operative image data for an object;
    a sampling unit coupled to the processor and configured to provide sample data corresponding to a view of the object; and
    a memory coupled to the processor and configured to execute a spherical harmonic transform and configured to identify a subspace corresponding to the object, and generate a reconstruction of the object based on the subspace and based on the sample data.

12. The system of claim 11 further including an output device coupled to the processor, the output device including at least one of a printer and a display.

* * * * *